United States Patent [19]

Alaimo

[11] 3,997,547
[45] Dec. 14, 1976

[54] PHENYLIMINO-2H-QUINOLIZINES

[75] Inventor: Robert J. Alaimo, Norwich, N.Y.

[73] Assignee: Morton-Norwich Products, Inc., Norwich, N.Y.

[22] Filed: July 14, 1975

[21] Appl. No.: 595,333

[52] U.S. Cl. .......................... 260/296 B; 424/263; 424/256
[51] Int. Cl.² ...................................... C07D 455/02
[58] Field of Search ................................ 260/296 B

[56] References Cited

UNITED STATES PATENTS

| | | | |
|---|---|---|---|
| 3,517,019 | 6/1970 | Alaimo | 260/294.8 |
| 3,763,174 | 10/1973 | Alaimo et al. | 260/296 B |
| 3,780,048 | 12/1973 | Alaimo et al. | 260/296 B |
| 3,933,836 | 1/1976 | Yale et al. | 260/296 R |

*Primary Examiner*—Natalie Trousof
*Assistant Examiner*—C. Jaisle
*Attorney, Agent, or Firm*—Anthony J. Franze

[57] ABSTRACT 2-(Substituted phenylimino)-2H-quinolizines are effective antiulcerogenic drugs.

7 Claims, No Drawings

PHENYLIMINO-2H-QUINOLIZINES

This invention relates to 2-(substituted phenylimino)-2H-quinolizines and particularly to those of the formula:

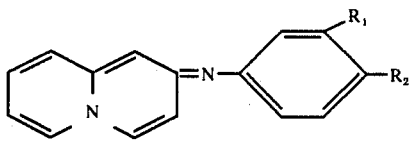

wherein $R_1$ is chloro, trifluoromethyl, methyl or hydrogen; $R_2$ is chloro, methyl, ethoxy or hydrogen. The invention also relates to a method for preparing them.

The compounds of this formula possess marked anti-ulcerogenic activity. When administered per os to pylorus ligated rats in doses of from 50–150 mg/kg, formation of ulcers is prevented and a reduction of asprin-induced ulceration in the stomach is elicited.

The method which is currently preferred for the preparation of the compounds of this invention consists in bringing together an appropriately substituted 2-(substituted anilino) quinolizinium bromide with a strong aqueous base such as sodium hydroxide in a suitable solvent such as water preferably under the influence of heat.

In order that this invention may be understood by and readily available to those skilled in the art the following illustrative examples are supplied.

EXAMPLE I 2-(3,4-Dichlorophenylimino)-2H-Quinolizine

A solution of 2-(3,4-dichloroanilino)quinolizinium bromide (23 g, 0.062 mole) in water (1 l.) was warmed to 50°. The warm solution was stirred and treated with a 2 N solution of NaOH (400 ml). The solution precipitated a yellow-orange product and the aqueous solution was warmed at 50° for 1 hour. After cooling and filtration the air dried product weighed 18 g (100%).

Recrystallization from ethyl acetate provided material which melted at 153°–155°.

Anal. Calcd. for $C_{15}H_{10}Cl_2N_2$: C, 62.30; H, 3.49; N, 9.69. Found: C, 62.50; H, 3.53; N, 9.68.

EXAMPLE II 2-(4-Chlorophenylimino)-2H-quinolizine

A suspension of 2-(4-chloroanilino)quinolizinium bromide (30 g., 0.09 mole) in 500 ml of 1N NaOH solution was warmed to 50° and stirred for 30 minutes. The crude product was removed by filtration and dried. The product (20 g., 87%) was recrystallized from ethanol to give material which melted at 183°–184°.

Anal. Calcd. for $C_{15}H_{11}ClN_2$: C, 70.73; H, 4.35; N, 11.00. Found: C, 70.71; H, 4.28; N, 10.90.

EXAMPLE III 2-(3-Trifluoromethylphenylimino)-2H-quinolizine

To a suspension of 2-(3-trifluoromethylanilino)-quinolizinium bromide (22 g., 0.060 mole) in $H_2O$ (400 ml) was added a solution of NaOH (25 g., 0.62 mole) in $H_2O$ (250 ml). The mixture was stirred at about 50° for 1 hour, then chilled and filtered. The yellow product weighed 17 g (97%). The sample was boiled in benzene, filtered and diluted with hexane. Evaporation of the solvent gave yellow crystals which melted at 134°–135°.

Anal. Calcd. for $C_{16}H_{11}F_3N_2$: C, 66.66; H, 3.85; N, 9.72. Found: C, 66.79; H, 3.89; N, 9.58.

EXAMPLE IV 2-(3-Chlorophenylimino)-2H-quinolizine Hydrate

To a suspension of 2-(3-chloroanilino)quinolizinium bromide (20 g, 0.06 mole) in water (500 ml) was added a solution of NaOH (30 g) in 250 ml of $H_2O$. The stirred mixture was warmed to 50° for about 1 hour. The mixture was then chilled, filtered and washed with cold $H_2O$. Recrystallization from ethanol provided 14 g (87% of orange colored product (m.p. 97°–100°) after drying sample at room temperature in vacuo.

Anal. Calcd. for $C_{15}H_{11}ClN_2 \cdot ¾ H_2O$: C, 67.16; H, 4.70; N, 10.45. Found: C, 67.27; H, 4.80; N, 10.30.

EXAMPLE V 2-(4-Ethoxyphenylimino)-2H-quinolizine

To a suspension of 2-(4-ethoxyanilino)quinolizium bromide (25 g, 0.07 mole) in $H_2O$ (500 ml) was added a solution of NaOH (25 g, 0.63 mole) in $H_2O$ (250 ml). The stirred mixture was warmed at 50° for about 1 hour, then chilled and filtered. The product was washed with water and air dried, then recrystallized from benzene with azetroping excess $H_2O$ and precipitating with hexane. The orange product weighed 19 g (100%) and melted at 157°–159°.

Anal. Calcd. for $C_{17}H_{16}N_2O$: C, 77.25; H, 6.10; N, 10.60. Found: C, 77.23; H, 5.96; N, 10.49.

EXAMPLE VI 2-(3,4-Dimethylphenylimino)-2H-quinolizine

A suspension of 2-(3,4-dimethylanilino)quinolizium bromide (33 g, 0.1 mole) in water (500 ml) was treated with sodium hydroxide (33 g, 0.82 mole) in water (350 ml). The mixture was stirred and warmed to 50°–60° for about 1 hour, then chilled and extracted with benzene (1 liter). The benzene solvent was removed in vacuo and the product recrystallization from benzene/(hexane) to yield 22 g (89%) m.p. 185°–187°.

Anal. Calcd. for $C_{17}H_{16}N_2$: C, 82.22; H, 6.49; N, 11.28. Found: C, 81.94; H, 6.34; N, 11.20.

What is claimed is:

1. A compound of the formula:

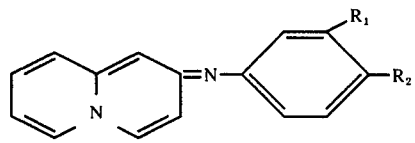

wherein $R_1$ is chloro, trifluoromethyl, methyl or hydrogen; $R_2$ is hydrogen, chloro, methyl or ethoxy.

2. The compound of claim 1 wherein $R_1$ is chloro; $R_2$ is chloro.

3. The compound of claim 1 wherein $R_1$ is chloro; $R_2$ is hydrogen.

4. The compound of claim 1 wherein $R_1$ is trifluoromethyl; $R_2$ is hydrogen.

5. The compound of claim 1 wherein $R_1$ is methyl; $R_2$ is methyl.

6. The compound of claim 1 wherein $R_1$ is hydrogen; $R_2$ is chloro.

7. The compound of claim 1 wherein $R_1$ is hydrogen; $R_2$ is ethoxy.

* * * * *